Figure 2:
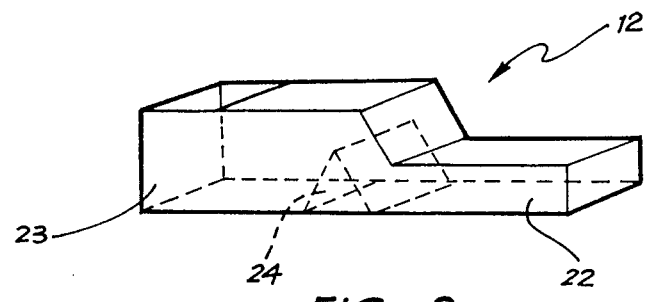

United States Patent [19]

Farrell et al.

[11] Patent Number: 4,640,896
[45] Date of Patent: Feb. 3, 1987

[54] WHOLE BLOOD CLOTTING TIMER

[75] Inventors: Peter C. Farrell, Pymble; Christopher D. Bertram, Coogee; Bruce K. Milthorpe, Naremburn; all of Australia

[73] Assignee: Unisearch Limited, Kensington, Australia

[21] Appl. No.: 514,828

[22] PCT Filed: Nov. 4, 1982

[86] PCT No.: PCT/AU82/00180
§ 371 Date: Jun. 28, 1983
§ 102(e) Date: Jun. 28, 1983

[30] Foreign Application Priority Data

Nov. 4, 1982 [AU] Australia ............................... PF1422

[51] Int. Cl.⁴ ...................... G01N 21/82; G01N 33/86
[52] U.S. Cl. ......................................... 436/34; 422/72; 422/73; 436/45; 436/69
[58] Field of Search ...................... 422/72, 73; 436/69, 436/45, 34, 805

[56] References Cited

U.S. PATENT DOCUMENTS

| | | | |
|---|---|---|---|
| 3,682,586 | 8/1972 | Ertingshausen et al. | 436/34 |
| 3,969,079 | 7/1976 | Catarious et al. | 422/73 |
| 4,030,834 | 6/1977 | Bauer et al. | 422/72 X |
| 4,202,665 | 5/1980 | Wenz et al. | 436/805 X |
| 4,226,537 | 10/1980 | Collys | 422/72 |
| 4,387,992 | 6/1983 | Swartz | 422/72 |

FOREIGN PATENT DOCUMENTS 2600377 12/1978 Australia .
908050 10/1962 United Kingdom .
1405694 9/1974 United Kingdom .

OTHER PUBLICATIONS

Tiffany et al., Analytical Chemistry, vol. 45, No. 9, Aug. 1973, pp. 1716-1723.

Primary Examiner—Arnold Turk
Attorney, Agent, or Firm—Holman & Stern, Chartered

[57] ABSTRACT

A method and device for determining the clotting time for a sample of whole blood. A sample of whole blood is placed in a cuvette (12) which is centrifuged in a centrifuge (11) to mix the blood sample with a coagulant in the cuvette (12) and simultaneously spin out the cells in the blood. The optical density of a part of the sample which is cleared of cells by the centrifugation is monitored using a light source (14) and a light detector (15) and the time measured for optical density indicative of clotting to be reached by a timer (25).

1 Claim, 2 Drawing Figures

U.S. Patent    Feb. 3, 1987    4,640,896

WHOLE BLOOD CLOTTING TIMER

CROSS-REFERENCE TO RELATED APPLICATIONS

This United States application stems from PCT International Application No. PCT/AU82/00180 filed Nov. 4, 1982.

The present invention relates to a whole blood clotting timer.

Clinically blood clotting timers are used to (a) investigate and diagnose disorders of the blood clotting system which concerns bleeding disorders such as failure to clot, or thrombosis, that is, excessive or uncontrolled clotting, or (b) monitor the efficacy of anticoagulation therapy either in treatment of potential thrombosis or in extracorporeal blood circulation such as takes place during haemodialysis or open heart surgery.

Blood clotting time estimations are conventionally carried out manually although attempts have been made to automate them. Attempts at automation have either involved mechanical or optical methods for the detection of the formation of a gel-like clot. Optical sensing must, however, be performed on blood plasma rather than whole blood. Plasma is obtained by removing red cells by mechanical means such as a filter or a centrifuge. This has required the blood sample to be treated to inhibit the clotting mechanism, to have the red blood cells removed and to then have the clotting mechanism reactivated. The clotting times of such reactivated samples differ systematically and greatly from those of whole blood mixed with activators, and the result is only available after an inconvenient delay.

The present invention relates to a device which combines the centrifugation and the optical sensing of clot formation into a single operation. This obviates the necessity to inhibit the clotting sequence thereby quickly giving activated clotting times on a par with those obtained mechanically from whole blood.

The present invention consists in a whole blood clotting timer comprising centrifuge means, means for mounting a whole blood sample within the centrifuge means, means to measure the optical density of the sample as the sample is being centrifuged, means to cause mixing of the whole blood sample with a blood clotting activator and means to measure the time between mixing of the blood with the clotting activator, or some other event which bears a reproducible time relationship with that event, and the time at which the centrifuged sample reaches a predetermined optical density or time rate of change of optical density or other optically pre-determined end-point corresponding to the time of clotting.

The present invention further consists in a method for determining the clotting time for a whole blood sample comprising mixing the blood with a blood clotting activator, centrifuging the mixture, measuring the optical density of a part of the mixture freed from blood cells as the mixture is centrifuged and measuring the time between the formation of the mixture, or some other event which bears a reproducible time relationship with that event, and the time at which optical density or time rate of change of optical density or other optical density criterion of the mixture reaches a predetermined level.

Centrifuges incorporating means for determining the optical density of a sample being centrifuged are known (see British Patent No. 1,405,694) however such centrifuges could not be used to measure the clotting time of whole blood and such centifuges do not include suitable timing means adapted to measure the time during which a predetermined change in the optical density of a sample occurs. The present invention lies in the realisation that by the incorporation of suitable timing means with a centrifuge having optical density determining means a rapid and convenient determination of blood clotting times for whole blood may be determined.

In a preferred embodiment of the present invention the blood sample is mounted within the centrifuge in a disposable cuvette. In this arrangement the cuvette preferably is so arranged that mixing of the blood sample and of an activator takes place by centrifugal action at a constant, and preferably very short time after the centrifuge is turned on. This arrangement firstly has the advantage that no non-disposable parts come in contact with the blood which eliminates a major source of timing error. This arrangement also allows the timer to be made quite small, allowing it to be readily transported to the patient. The simplicity of operation allows general nursing staff and, in the case of home haemodialysis patients, members of the public to use it with little training being required.

In preferred embodiments of the invention the cuvette used to hold the sample is at least transparent in a region inwardly of that end which is radially outermost when mounted in the centrifuge. This region of the cuvette should coincide in use with a transparent window in the rotor to allow a light beam to shine through the cuvette and its contents once on each revolution of the centrifuge. The optical density of the sample can thus be determined by measuring the amount of light transmitted through the sample. Means need to be provided to ensure that the light transmittance is measured while the sample is in the light beam. This may be conveniently achieved by the use of a locating tab on the rotor intersecting another light beam to trigger the taking of an optical density reading.

The centrifuge may be of any suitable type, however, an electrically driven centrifuge rotating at up to 6000 rpm has been found to be most suitable. The timing means and optical density determining means may be of any suitable type known in the art. Solid state electronic timing means are most conveniently used.

In order to obtain as consistent results as possible it is desirable for the sample to be maintained at a predetermined temperature, most preferably 37° C., during the determination of the clotting time. If desired multiple determinations could be carried out simultaneously by having a plurality of samples being simultaneously or sequentially examined.

Figure 1:
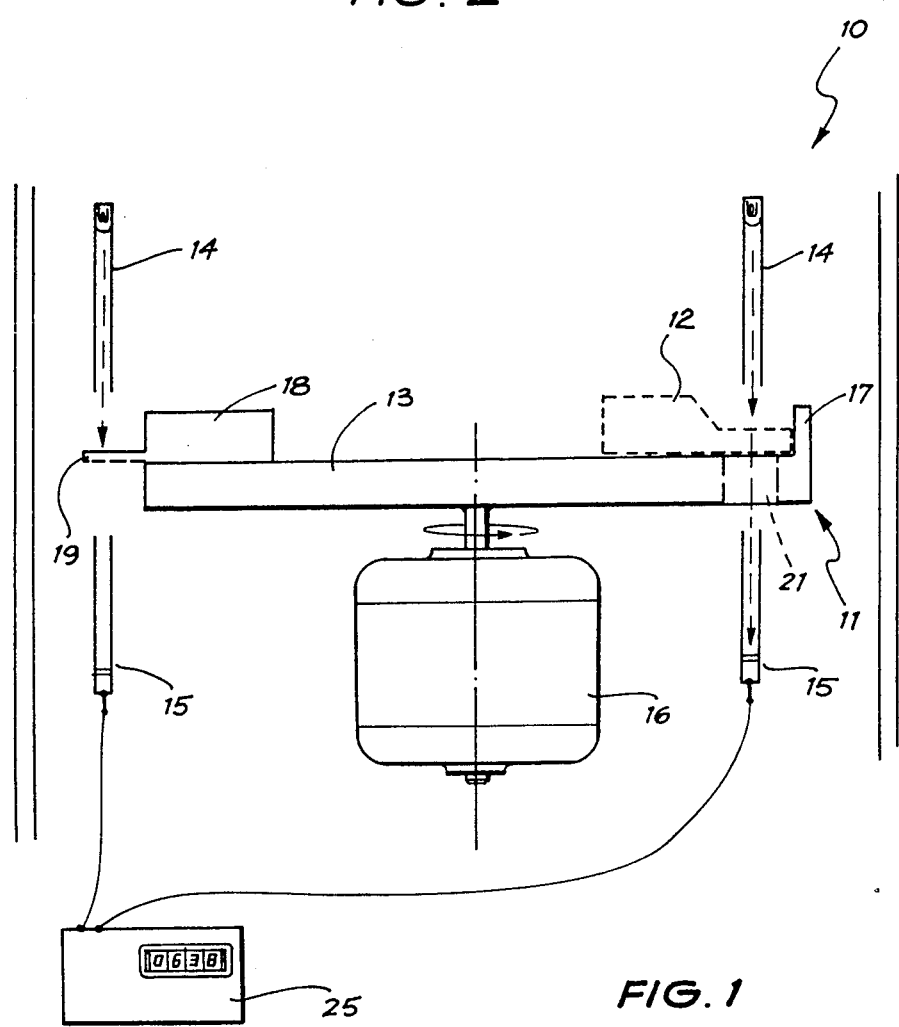

Hereinafter given by way of example only is a preferred embodiment of the present invention described with reference to the accompanying drawings in which:

FIG. 1 is a diagrammatic cross sectional view through the centrifuge section of a whole blood clotting timer according to the present invention; and FIG. 2 is a perspective view of a cuvette for use in the centrifuge of FIG. 1.

The whole blood clotting timer 10 comprises a centrifuge 11, a cuvette 12 adapted to hold a blood sample and mountable on the rotor 13 of the centrifuge 11, a pair of collimating light sources 14 and corresponding light intensity detectors 15 and timing means 25.

The rotor 13 is driven by an electric motor 16 which runs at 6000 rpm. The cuvette 12 is retained on the rotor 13 by a cuvette holder 17. The weight of the cuvette 12 on the rotor is balanced by a diametrically opposed counter weight 18 from which projects a locating tab 19.

One collimated light source 14 is so disposed that it is vertically above the cuvette path such that the light beam will pass through a part of the cuvette spaced inwardly of its radially outer end, so as to avoid the beam being obscured by cells thrown to the end of the cuvette by centrifugal action, and through a window 21 in the rotor 13. The intensity of the beam is measured by a corresponding one of the light detectors 15 and a signal fed, through means not shown, to the timer to cause the timer to stop when a predetermined time rate of change of optical density has been reached by the sample.

The timing of the reading of the optical density of the sample in the cuvette 12 is achieved by taking a reading as the tab 19 intersects the beam of the other light source 14.

In use a clotting activator such as thrombin is placed in an outer chamber 22 of the cuvette 12 and the cuvette placed in position on the rotor 13. The blood sample is introduced into an inner chamber 23 and the centrifuge started which simultaneously starts the timing means. Centrifugal action substantially instantaneously forces the blood sample from the inner chamber 23 over a ridge 24 in the cuvette and into the outer chamber 22 with sufficient force to ensure complete mixing of the blood and the clotting activator. The blood cells then rapidly settle at the outer edge of the sampling chamber leaving a region of clear plasma for interrogation by the light beam. A reduction in the intensity of the light transmitted through the plasma to the detector 15 signals the onset of clotting and the timer is turned off. The time between the switching on and switching off of the centrifuge is then displayed on the timing means.

What is claimed is:

1. A method for determining the clotting time for a whole blood sample comprising inserting the whole blood sample into a first, radially inner compartment of a disposable cuvette in a centrifuge, inserting a blood clotting activator into a second, radially outer compartment of that cuvette which is separated from the first compartment by a ridge in the floor of the cuvette, actuating the centrifuge to cause the whole blood sample to flow radially outwardly over the ridge and to mix with the blood clotting activator in a second compartment and simultaneously starting timing means running, continuing the operation of the centrifuge to sediment the blood cells against a radially outer wall of the second compartment, periodically measuring the optical density of a part of the mixture in the second compartment radially inwardly of said wall thereof which part of the mixture is freed from blood cells, stopping the timing means when the optical density or the time rate of change of the optical density of the mixture reaches a predetermined level, thereafter stopping the centrifuge and indicating the time interval between the starting and stopping of the timing means.

* * * * *